(12) United States Patent
Kave et al.

(10) Patent No.: US 8,277,453 B2
(45) Date of Patent: Oct. 2, 2012

(54) INSTRUMENTS AND SYSTEMS FOR VERTEBRAL COLUMN MANIPULATION

(75) Inventors: Douglas D Kave, Byhalia, MS (US);
Paula A Nichter, Memphis, TN (US);
Paul Wheeler, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 477 days.

(21) Appl. No.: 12/609,162

(22) Filed: Oct. 30, 2009

(65) Prior Publication Data

US 2011/0106082 A1    May 5, 2011

(51) Int. Cl.
*A61B 17/70*    (2006.01)

(52) U.S. Cl. ...................................... 606/86 A; 606/914

(58) Field of Classification Search ............... 606/86 A, 606/246, 279, 914, 916
See application file for complete search history.

(56) References Cited

U.S. PATENT DOCUMENTS

| | | | |
|---|---|---|---|
| 4,409,968 A | 10/1983 | Drummond | |
| 4,505,268 A | 3/1985 | Sgandurra | |
| 5,020,519 A | 6/1991 | Hayes et al. | |
| 5,102,412 A | 4/1992 | Rogozinski | |
| 5,176,679 A | 1/1993 | Lin | |
| 5,181,917 A | 1/1993 | Rogozinski | |
| 5,196,013 A | 3/1993 | Harms et al. | |
| 5,261,907 A | 11/1993 | Vignaud et al. | |
| 5,281,223 A | 1/1994 | Ray | |
| 5,385,565 A | 1/1995 | Ray | |
| 5,425,732 A | 6/1995 | Ulrich | |
| 5,437,669 A | 8/1995 | Yuan et al. | |
| 5,478,340 A | 12/1995 | Kluger | |
| 5,527,310 A * | 6/1996 | Cole et al. | ...................... 606/60 |
| 5,531,747 A | 7/1996 | Ray | |
| 5,545,166 A | 8/1996 | Howland | |
| 5,591,165 A | 1/1997 | Jackson | |
| 5,632,744 A | 5/1997 | Campbell, Jr. | |
| 5,649,926 A | 7/1997 | Howland | |
| 5,672,175 A | 9/1997 | Martin | |
| 5,702,392 A | 12/1997 | Wu et al. | |
| 5,702,457 A | 12/1997 | Walch et al. | |
| 5,704,937 A | 1/1998 | Martin | |
| 5,707,371 A | 1/1998 | Metz-Stavenhagen | |
| 5,733,284 A | 3/1998 | Martin | |
| 5,797,910 A | 8/1998 | Martin | |
| 5,814,046 A | 9/1998 | Hopf | |
| 6,015,409 A | 1/2000 | Jackson | |

(Continued)

FOREIGN PATENT DOCUMENTS

DE    8712943 U1    11/1987

(Continued)

*Primary Examiner* — Kevin T Truong
*Assistant Examiner* — Larry E Waggle, Jr.

(57) ABSTRACT

Vertebral column manipulation systems include spinal derotation instrumentation to affect one or more derotation maneuvers on a scoliotic spine or on a spine having one or more displaced, misaligned or curved vertebral levels. Derotation instrumentation is attached to at least one vertebral body, with the instrumentation including at least two elongated extensions mounted to and extending proximally from the at least one vertebral body. A linking assembly extends between and links proximal ends of the extensions to one another. The linking assembly includes first and second mounting assemblies movably engaged to an elongate link member extending transversely to the extensions. Each of the mounting assemblies includes a movable joint for receiving the proximal end of a respective one of the extensions and a cam assembly for securing the mounting assembly in position relative to the link member and to fix the joint around the extension.

13 Claims, 10 Drawing Sheets

U.S. PATENT DOCUMENTS

| | | |
|---|---|---|
| 6,090,113 A | 7/2000 | Le Couedic et al. |
| 6,171,311 B1 | 1/2001 | Richelsoph |
| 6,251,112 B1 | 6/2001 | Jackson |
| 6,402,753 B1 | 6/2002 | Cole et al. |
| 6,458,131 B1 | 10/2002 | Ray |
| 6,511,484 B2 | 1/2003 | Torode et al. |
| 6,530,929 B1 | 3/2003 | Justis et al. |
| 6,565,568 B1 | 5/2003 | Rogozinski |
| 6,605,088 B1 | 8/2003 | St. Onge et al. |
| 6,648,888 B1 | 11/2003 | Shluzas |
| 6,749,613 B1 | 6/2004 | Conchy et al. |
| 6,755,828 B2 | 6/2004 | Shevtsov et al. |
| 6,916,319 B2 | 7/2005 | Munting |
| 6,945,933 B2 | 9/2005 | Branch et al. |
| 7,004,947 B2 | 2/2006 | Shluzas et al. |
| 7,090,679 B2 | 8/2006 | Saint-Martin et al. |
| 7,188,626 B2 | 3/2007 | Foley et al. |
| 7,520,879 B2 | 4/2009 | Justis et al. |
| 2003/0144665 A1 | 7/2003 | Munting |
| 2003/0225408 A1 | 12/2003 | Nichols et al. |
| 2004/0034350 A1 | 2/2004 | St. Onge et al. |
| 2004/0172022 A1 | 9/2004 | Landry et al. |
| 2004/0249378 A1 | 12/2004 | Saint Martin et al. |
| 2005/0033291 A1 | 2/2005 | Ebara |
| 2005/0033299 A1 | 2/2005 | Shluzas |
| 2005/0149036 A1 | 7/2005 | Varieur et al. |
| 2005/0149053 A1 | 7/2005 | Varieur et al. |
| 2005/0159757 A1 | 7/2005 | Shluzas et al. |
| 2005/0171540 A1 | 8/2005 | Lim et al. |
| 2005/0182400 A1 | 8/2005 | White |
| 2005/0245928 A1 | 11/2005 | Colleran et al. |
| 2006/0106380 A1 | 5/2006 | Colleran et al. |
| 2006/0200132 A1* | 9/2006 | Chao et al. ........................ 606/61 |
| 2007/0049931 A1 | 3/2007 | Justis et al. |
| 2007/0093846 A1 | 4/2007 | Frigg et al. |
| 2007/0161989 A1 | 7/2007 | Heinz et al. |
| 2007/0173827 A1 | 7/2007 | Morrison et al. |
| 2007/0213715 A1* | 9/2007 | Bridwell et al. ................. 606/61 |
| 2007/0213716 A1 | 9/2007 | Lenke et al. |
| 2008/0097441 A1* | 4/2008 | Hayes et al. ..................... 606/64 |
| 2008/0172062 A1* | 7/2008 | Donahue et al. ............. 606/104 |
| 2008/0319477 A1 | 12/2008 | Justis et al. |
| 2011/0172714 A1* | 7/2011 | Boachie-Adjei et al. ..... 606/264 |

FOREIGN PATENT DOCUMENTS

| | | |
|---|---|---|
| EP | 0528177 A2 | 2/1993 |
| EP | 0602351 A1 | 6/1994 |
| EP | 1269930 A2 | 1/2003 |
| WO | 9002527 A1 | 3/1990 |
| WO | 9106254 A1 | 5/1991 |
| WO | 02094114 A1 | 11/2002 |
| WO | 2005058141 A2 | 6/2005 |

* cited by examiner

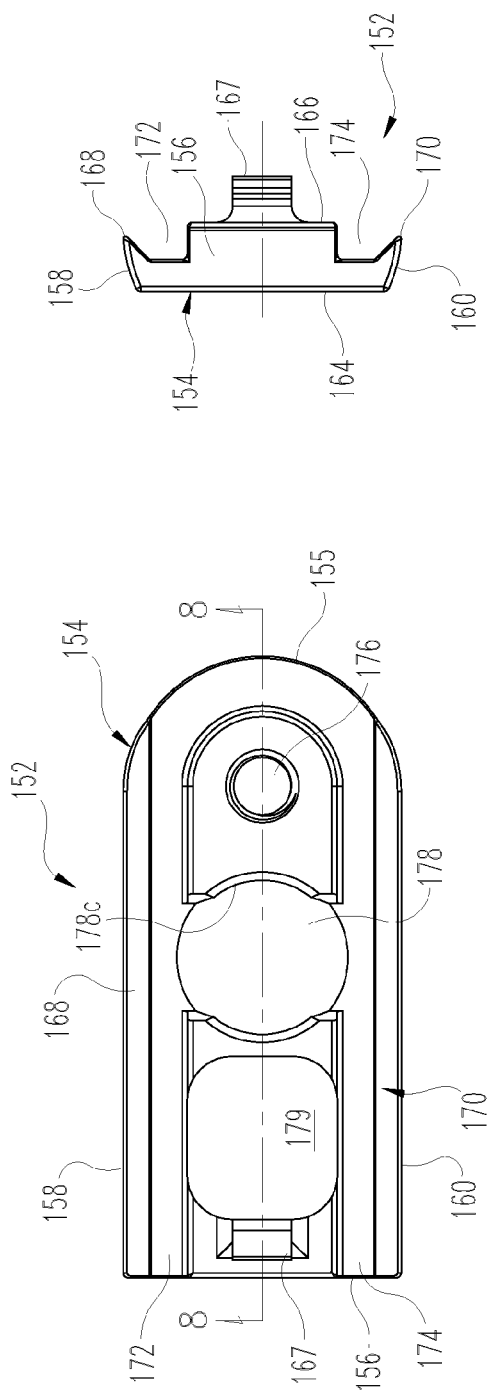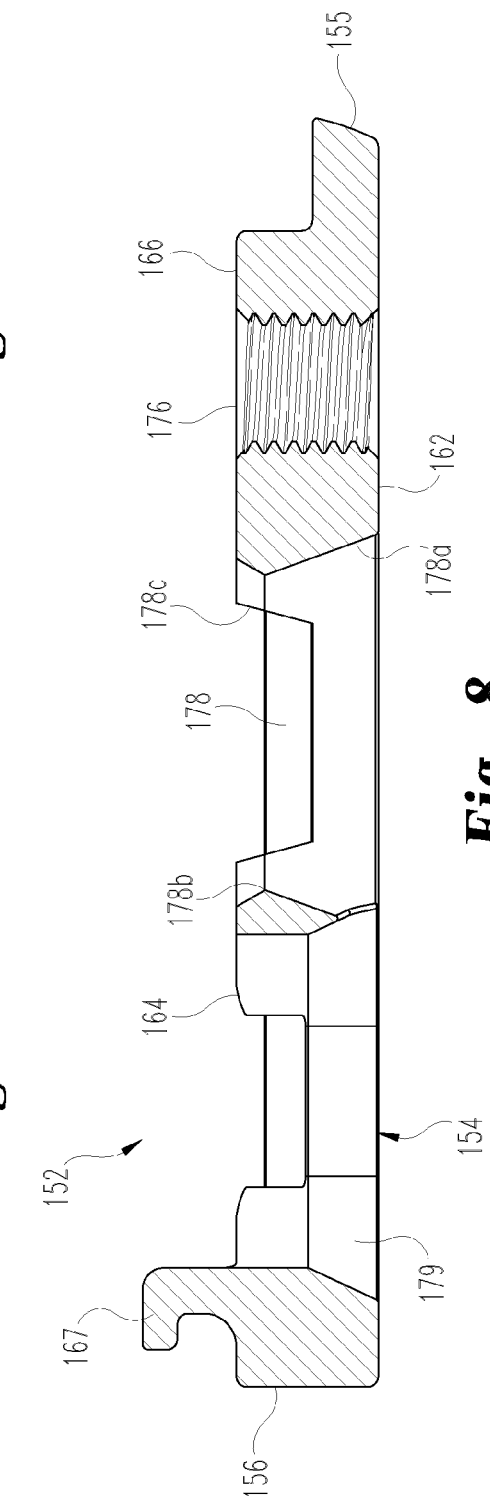

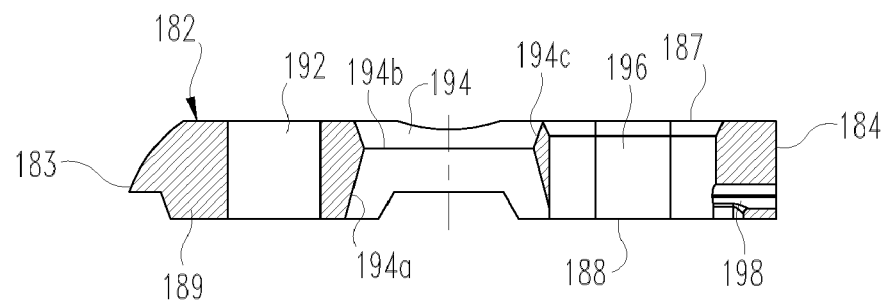
Fig. 13
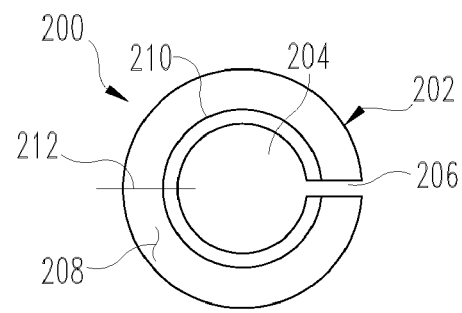
Fig. 14
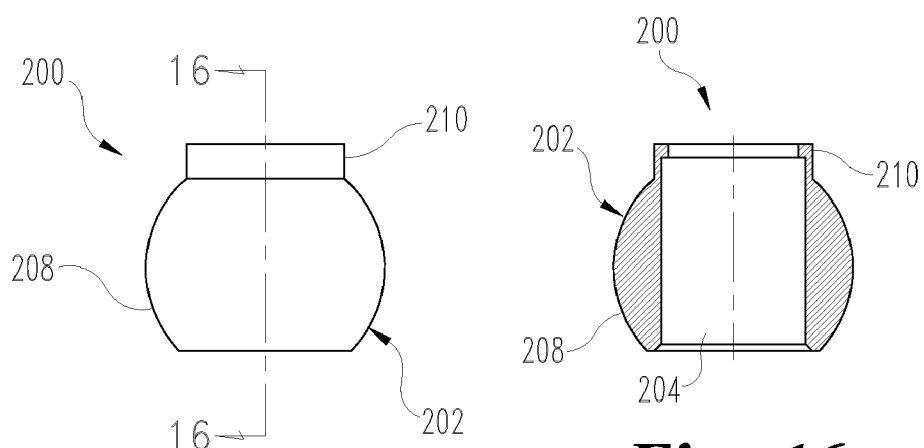
Fig. 15
Fig. 16

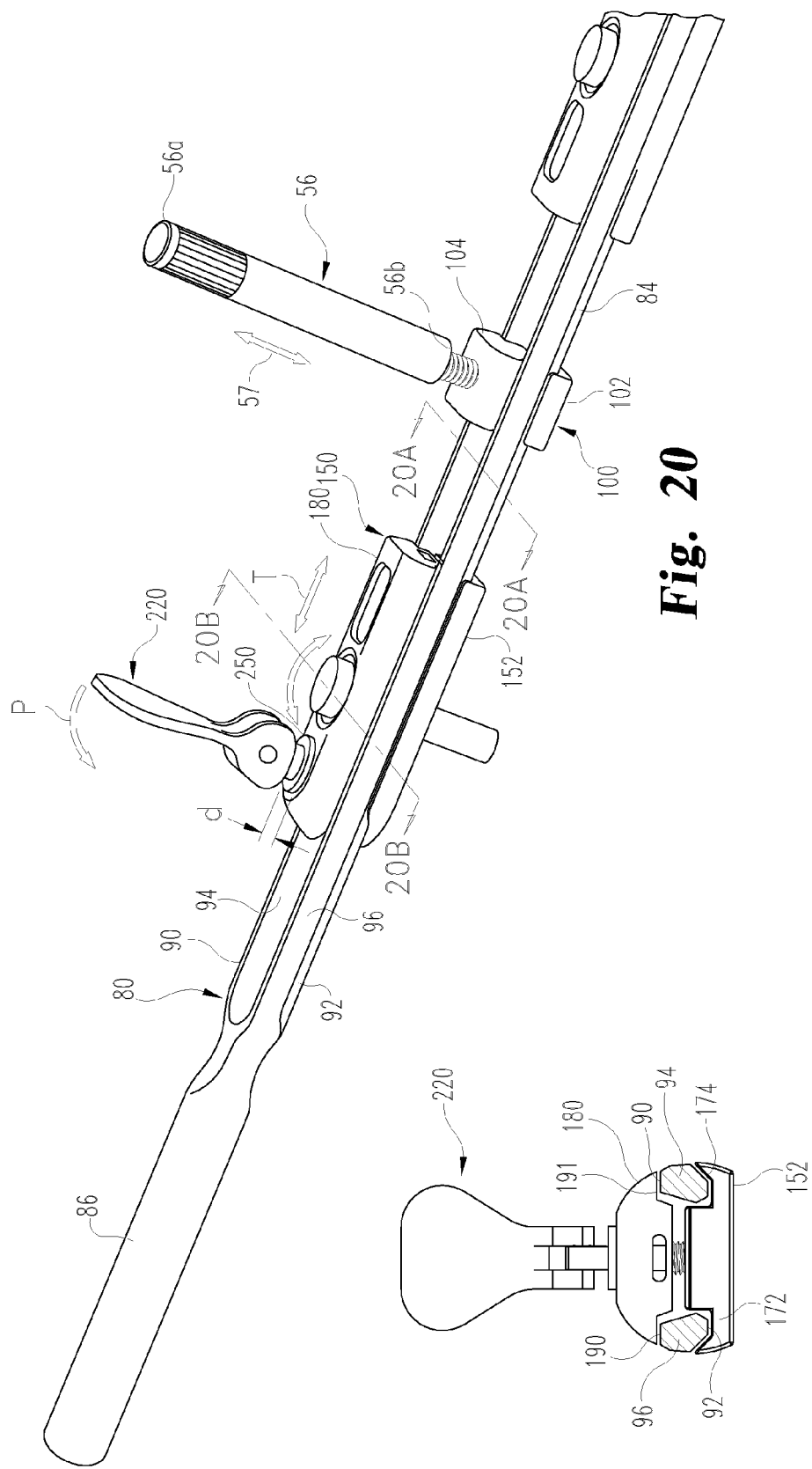

INSTRUMENTS AND SYSTEMS FOR VERTEBRAL COLUMN MANIPULATION

BACKGROUND

Surgical correction of the positioning and alignment of one or more vertebrae in the spinal column can be desired to address various pathologies and conditions of patients. However, such repositioning and re-alignment can be time-consuming, cumbersome, and potentially difficult to achieve during a surgical procedure. For example, the alignment of multiple vertebral levels can require manipulation of instrumentation at each level to achieve the desired results. Forces applied to the vertebral body need to be controlled to minimize stresses on the vertebral bodies and implants. Furthermore, the alignment at one level may need to be maintained while other levels are aligned. In addition, the instrumentation employed to achieve the alignment can hinder placement of stabilization constructs that post-operatively maintain the corrected positioning and alignment achieved during surgery.

Existing vertebral column manipulation systems include many components and can be fiddlesome for the surgeon to use during the procedure. In addition, the systems are not employed or readily employed in minimally invasive surgical procedures, but rather involve open procedures that completely expose the affected segments of the spinal column. Therefore, instruments, methods and systems that facilitate surgical correction of the alignment and positioning of a vertebra or vertebrae of the spinal column would be desirable. Furthermore, instruments, methods and systems that facilitate placement of stabilization constructs that post-operatively maintain the corrected vertebra or vertebrae are also desirable. In addition, instruments, methods and systems that facilitate control of the stress exerted on implants and vertebrae to which the implants are attached would be desirable.

SUMMARY

Vertebral column manipulation systems include spinal derotation instrumentation to affect one or more derotation maneuvers on a scoliotic spine or on a spine having one or more displaced, misaligned or curved vertebral levels. Derotation instrumentation is attached to at least one vertebral body, with the instrumentation including at least two elongated extensions mounted to and extending proximally from the at least one vertebral body. A linking assembly extends between and links proximal ends of the extensions to one another. The linking assembly includes first and second mounting assemblies movably engaged to an elongate linking member extending transversely to the extensions. Each of the mounting assemblies includes a movable joint for receiving the proximal end of a respective one of the extensions and a cam assembly for securing the mounting assembly in position relative to the link member and to fix the movable joint in position relative to the link member and to the extension.

According to one aspect, a system for correcting alignment of one or more vertebrae of a spine includes first and second implants engageable to one of the one or more vertebrae, first and second stabilization elements positionable along the spine and engageable to respective one of the first and second implants, and a derotation instrument set. The derotation instrument set includes first and second elongated implant extensions with distal end portions releasably engaged to respective ones of the first and second implants and extending proximally from the distal portion to an opposite proximal end portion. The derotation instrument set also includes a transverse linking assembly positioned between and engaged to each of the first and second implant extensions at the proximal end portions. The transverse linking assembly includes an elongate link member with a central plate portion extending between the proximal end portions of the implant extensions, a derotation handle engaged to the central plate portion, and first and second mounting assemblies engaged to the central plate portion and to the proximal end portion of a respective one of the first and second implant extensions. The mounting assemblies each include first and second plate members along opposite sides of the central plate portion and a pivotable ball member captured between the first and second plate members that receive the proximal end portion of the respective extension.

According to another aspect, the system includes a derotation instrument set that includes first and second elongated implant extensions with distal end portions releasably engaged to respective ones of first and second implants that extend from the distal portion an opposite proximal end portion and a transverse linking assembly positioned between and engaged to each of the first and second implant extensions at the proximal end portions. The transverse linking assembly includes an elongate link member with a slot and a pair of side members extending along opposite sides of the slot, and a derotation handle engaged to the link member along the slot. The transverse linking assembly also includes first and second mounting assemblies engaged to the link member on opposite sides of the derotation handle. The first and second mounting assemblies each include a pivotable joint in the slot receiving the proximal end portion of a respective one of the first and second implant extensions through the slot of the link member.

According to another aspect, a derotation instrument set includes a link assemble engageable to proximal ends of anchor extensions with mounting assemblies mounted to a link member. Each of the mounting assemblies includes first and second plate members that have a rounded first end wall and an opposite linear second end wall and the first and second end walls extend between opposite sidewalls that extending along the link member. The first plate member defines a non-threaded hole and the second plate member defines a threaded hole aligned with the non-threaded hole adjacent the first end walls of the first and second plate members. The first and second plate members also define aligned through-holes adjacent the second end walls and aligned receptacles located between the aligned through-holes and the aligned non-threaded and threaded holes. The mounting assemblies also include a cam assembly with a post extending through the non-threaded hole and threadingly engaged to the threaded hole; a pivotable ball member captured between the first and second plate members in the aligned receptacles; and a hook member extending from the second plate member into the through-hole of the first plate member, the hook member further extending into a slot extending from the through-hole of the first plate member through the second end wall of the first plate member.

These and other aspects will also be apparent from the following description and the Figures.

BRIEF DESCRIPTION OF THE DRAWINGS

FIG. 6 is a plan view of the upper surface of the bottom plate of the extension linking assembly of FIG. 2.

FIG. 7 is an end elevation view of the bottom plate of FIG. 6.

FIG. 8 is a section view along line 8-8 of FIG. 6.

FIG. 13 is a section view through line 13-13 of FIG. 9.

FIG. 14 is a plan view of a ball member of the extension linking assembly of FIG. 2.

FIG. 15 is an elevation view of the ball member of FIG. 14.

FIG. 16 is a section view along line 16-16 of FIG. 15.

FIG. 20 is a perspective view of the extending linking assembly with the cam assembly in a disengaged position allowing the mounting member to move along the plate.

FIG. 20A is a section view along line 20A-20A of FIG. 20.

DESCRIPTION OF THE ILLUSTRATED EMBODIMENTS

Figure 1:
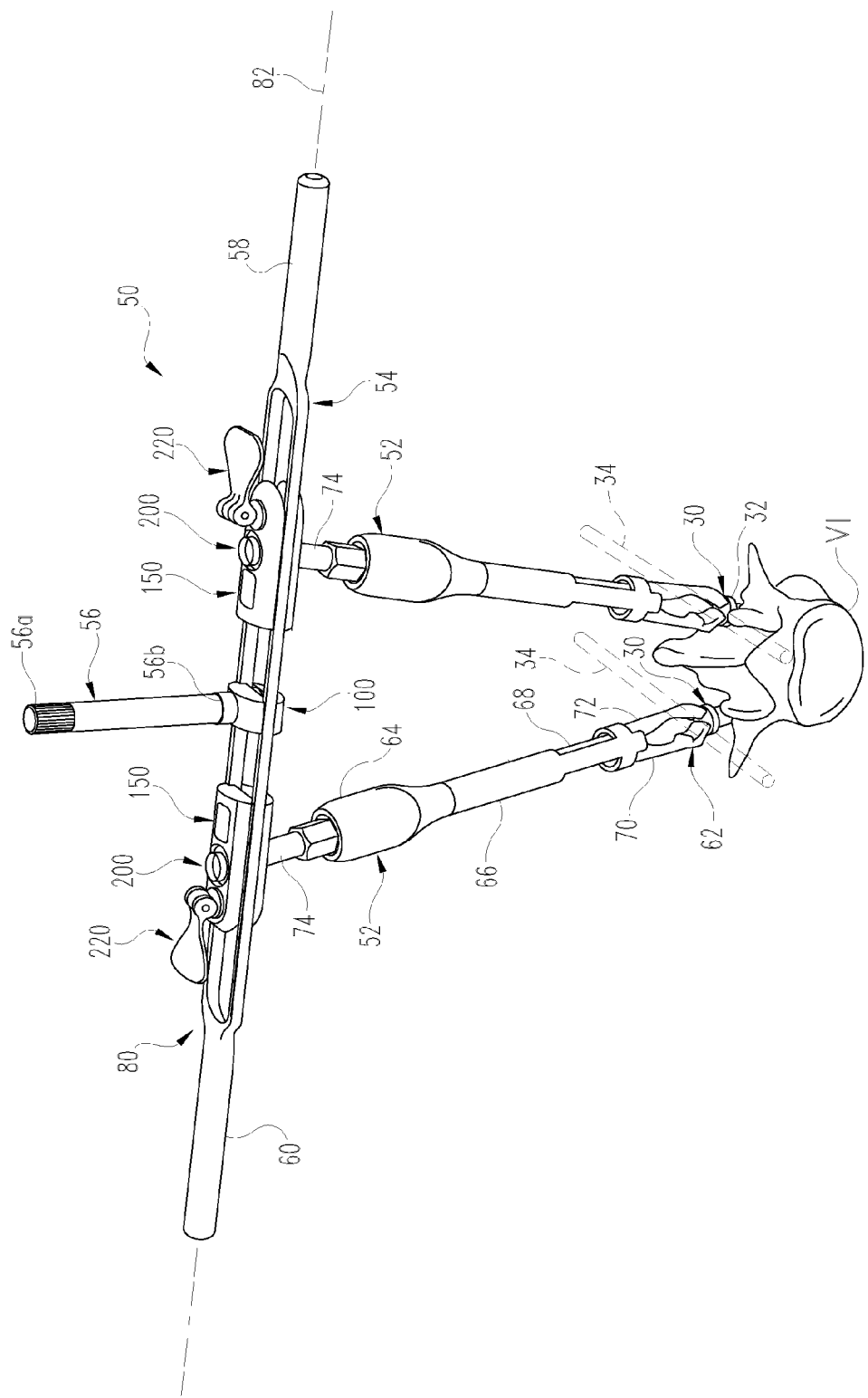
FIG. 1 is a perspective view of a derotation system coupled to implants engaged to a vertebra.

For the purpose of promoting an understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

Vertebral column manipulation systems include spinal derotation instrumentation to affect one or more derotation maneuvers on a scoliotic spine or on a spine having one or more displaced, misaligned or curved vertebral levels. Derotation instrumentation is attached to at least one vertebral body, with the instrumentation including at least two elongated extensions mounted to and extending proximally from the at least one vertebral body. A linking assembly extends between and links proximal ends of the extensions to one another. The linking assembly includes first and second mounting assemblies movably engaged to an elongate link member such as a plate with the elongate link member extending transversely to the extensions. Each of the mounting assemblies includes a ball joint for receiving the proximal end of a respective one of the extensions and a cam assembly for securing the mounting assembly in position relative to the link member and to clamp the ball joint around the extension. At least one derotation handle is movably connected with the linking assembly between the extensions in transverse relation to the link member and extending generally in the same direction as the extensions so that manipulation of the handle simultaneously manipulates the vertebra or vertebrae to which the extensions are mounted.

The derotation instrumentation includes at least two extensions that are attached to left, right, or left and right sides of one or more vertebrae of the spinal column. In addition, two or more derotation instrumentation sets can be connected to one another with a bridge member extending between and engaged to the derotation instrument sets to provide an interconnected derotation system spanning multiple vertebrae and multiple vertebral levels. As a result, the surgeon may manipulate an integrated frame assembly to affect derotation across multiple vertebral levels, rather than separately manipulating several derotation instrument sets to effect derotation of each vertebra or individual vertebral level. The derotation instrument assembly may also include a secondary handle, either alone or in combination with the derotation handle, extending laterally from one or both ends of the linking assembly to provide further vertebral manipulation options to the surgeon.

The extensions are removably engaged to bone implants. The bone implants can be configured as pedicle screws, with each screw having a head portion which includes a pair of arms defining a channel for receiving a spinal stabilization element such as a rod, and with the arms defining threads for other suitable engaging structure receiving a set screw, nut, cap or other device for capturing the spinal rod within the channel. The screw can be uni-axial, fixed-angle, or multi-axial so that the head can pivot relative to the bone engaging portion. In the illustrated embodiment of FIG. 1, the head portions of the screws are configured to receive stabilization elements either through a top opening between the pair of arms or to receive an end of the stabilization element as it is passed through the head in an end-wise manner. In another embodiment, the head portion of the screws opens to a side so that the stabilization element can be side-loaded therein. Other embodiments contemplate any suitable type of implant that can be engaged to a vertebra and coupled to an elongated stabilization element that extends along two or more vertebrae.

The elongate extensions can each include a distal end portion configured for selective clamping to one arm of the screw head portion or to both arms of the screw head portion. In one specific embodiment, the implant holder includes a tubular body extending the length of the implant holder and a clamp portion extending from the distal end of the tubular body to clampingly engage the head of the screw. The proximal end of the extension includes an elongate member that extends into the ball joint so that the linking assembly is rotatably and pivotally coupled to the extension to allow for angular adjustment therebetween. The engagement between the extensions and the linking assembly provides mounting assemblies that are movable along the link member for variable lateral adjustment of the mounting assemblies to accommodate the spacing between the proximal ends of the extensions, and the ball joints in the mounting assemblies are pivotal within the mounting assemblies to provide variable angular positions within the mounting assemblies so that the linking assembly can be engaged to the extensions at various orientations of the extensions relative to one another and at carious orientations of the extensions relative to the link member. The mounting assemblies each include a cam assembly that can be readily accessed and manipulated by the surgeon to lock and release the linking assembly from the proximal ends of the extensions.

In one embodiment, the link member is configured with an elongate central plate portion defining an elongate slot extending therethrough and cylindrical post portions extending outwardly from opposite ends of the central plate portion and in opposite directions from one another. The cylindrical post portions can be employed as handles to assist in manipulating the derotation system, and/or can be engaged by a bridge extending between derotation instrumentation sets.

In instances requiring derotation across multiple vertebral levels, multiple derotation instrumentation sets can be attached to respective ones of the multiple vertebral bodies requiring derotation, with the derotation instrumentation sets interconnected by an inter-level bridging assembly coupled between the individual derotation instrument sets. The transverse bridge assembly can be releasably coupled directly to the extensions, directly to the primary handle, and/or directly to the linking assembly.

In FIG. 1 there is shown one embodiment of derotation instrumentation assembly coupled to implants 30. Implants 30 are engaged to a vertebral body V1. In one specific application, implants 30 are bone anchors secured to respective ones of the pedicles of vertebral body V1. Implants 30 each include a receiver portion 32 for receiving a respective elongated spinal stabilization element 34 positionable along the spinal column and securable to the implants to maintain a positioning of one or more vertebral bodies. In the illustrated embodiment, the implants are bone screws with a U-shaped head portion providing a receiver to receive a spinal rod. Other embodiments contemplate saddles, posts, clamping members, side-loading members or other receiver type members extending from a bone engaging portion in the form of a staple, hook, screw, interbody device, intrabody device or other bone engaging member.

Derotation instrumentation 50 includes implant extensions 52 removably engaged to respective ones of the implants 30 and extending proximally therefrom. The implant extensions 52 can be interconnected with one another in a bilateral fashion with a transverse linking assembly 54 extending therebetween. Transverse linking assembly 54 includes a primary derotation handle 56 extending therefrom at a location between implant extensions 52. Primary derotation handle 56 extends in a direction that is generally in the same direction as implant extensions 52 away from the spinal columns and in a direction that is generally parallel to the sagittal plane of the spinal column. Secondary derotation handles 58, 60 are provided at opposite ends of transverse linking assembly 54. Thus, secondary derotation handles 58, 60 extend in a transverse orientation to implant extensions 52 and in a direction that is generally parallel to the coronal plane of the spinal column.

Derotation instrumentation 50 can be manipulated with one or both of primary handle 56 and secondary handles 58, 60 to displace, pull, twist or align the vertebra to which implants 30 is engaged into the desired alignment with the spinal column. Accordingly, manipulation of multiple anchors engaged to the spinal column can be completed with a single-handled approach, although the application of such forces through multiple handles is not precluded. For example, positioning of primary handle 56 in a medial or central relation relative to the implants 30 results in the corrective forces being distributed to both implants 30 and thus to multiple locations on the vertebra V1. This can reduce stress concentrations at any single bone/implant interface as the manipulation forces are applied.

It is further contemplated that a number of derotation instrumentation sets 50 can be coupled to one another by one or more inter-level bridge members extending between and coupled to, for example, primary handles 56 of each of the instrumentation sets 50. The inter-level, linked instrumentation sets 50 provide a multi-level vertebral derotation system that facilitates the application of and distribution of derotation, correction, alignment and other forces to various bony structures engaged by the bone implants and interconnected within the system. Accordingly, the resultant stress on any one of the implants and the bone to which the implant is engaged is distributed to multiple locations and/or multiple vertebrae. It is contemplated that any one or two more vertebral levels with derotation instrumentation sets 50 can be linked. It is further contemplated that any subset of instrumented vertebral levels in a system could be linked. In addition or in lieu of linking primary handles 56, secondary handles 58, 60, linking assembly 54, and/or implant extensions 52 could be linked with an inter-level bridge member.

One specific example of implant extension 52 is shown. Implant extension 52 includes an elongated body assembly 60 extending between a distal portion 62 engaged to bone anchor 30 and a proximal portion 64 engaged to linking assembly 54. Body assembly includes an outer tubular member 66 extending around an inner member 68. Inner member 68 includes a pair of movable clamping arms 70, 72 forming distal portion 62 that are clamped to opposite sides of anchor 30. Outer member 66 is movable proximally and distally along inner member 68 to hold arms 70, 72 in clamping engagement with anchor 30 in the distal position and to allow clamping arms 70, 72 to move away from one another and release anchor 30 in the proximal position. Clamping arms 70, 72 are extend distally from the distal end of outer member 66 and proximally from the proximal end of anchor 30 to form a space to receive stabilization element 34 between clamping arms 70, 72 and proximally of anchor 30. Furthermore, from the relative positions shown in FIG. 1, outer member 66 is movable distally toward anchor 30 with clamping arms 70, 72 engaged to anchor 30 to reduce or position the stabilization element 34 into anchor 30, and to assist in aligning vertebra V1 with the adjacent vertebral bodies. Further examples of suitable implant extensions are provided in U.S. Pat. No. 6,530,929 issued Mar. 11, 2003; U.S. Pat. No. 7,188,626 issued Mar. 13, 2007; U.S. Pat. No. 7,520,879 issued Apr. 21, 2009; U.S. Patent App. Pub. No. 2005/0171540 published on Aug. 4, 2005; U.S. Patent App. Pub. No. 2007/0049931 published on Mar. 1, 2007; U.S. Patent App. Pub. No. 2007/0213715 published on Sep. 13, 2007; U.S. Patent App. Pub. No. 2007/0213716 published on Sep. 13, 2007; and U.S. Patent App. Pub. No. 2008/0319477 published on Dec. 5, 2008; each of which is incorporated herein by reference in its entirety.

Implant extensions 52 also each include a coupling member 74 extending axially and proximally from body assembly 60 to linking assembly 54. As discussed further below, coupling member 74 is positioned in a ball joint of one of the mounting assemblies 150 of linking assembly 54. Member 74 can be formed as a proximal extension of inner member 68, a proximal extension of outer body 66, or as a separate member attached to one or both of inner and outer members 68, 66. Member 74 can be formed as a sleeve that includes a central passage extending therethrough and opening at the proximal end of member 74 that aligns with a passage body assembly 60 opening between arms 70, 72. The passage can accommodate insertion of implants or instruments through implant extension 52 to facilitate in manipulating anchor 30, the spinal stabilization element 34, and/or an engaging member to secure the stabilization element 34 to implant 30. It is also contemplated that biologic agents, bone cement, therapeutic agents or other spinal treatment agent or device could be placed through the passage.

Figure 2:
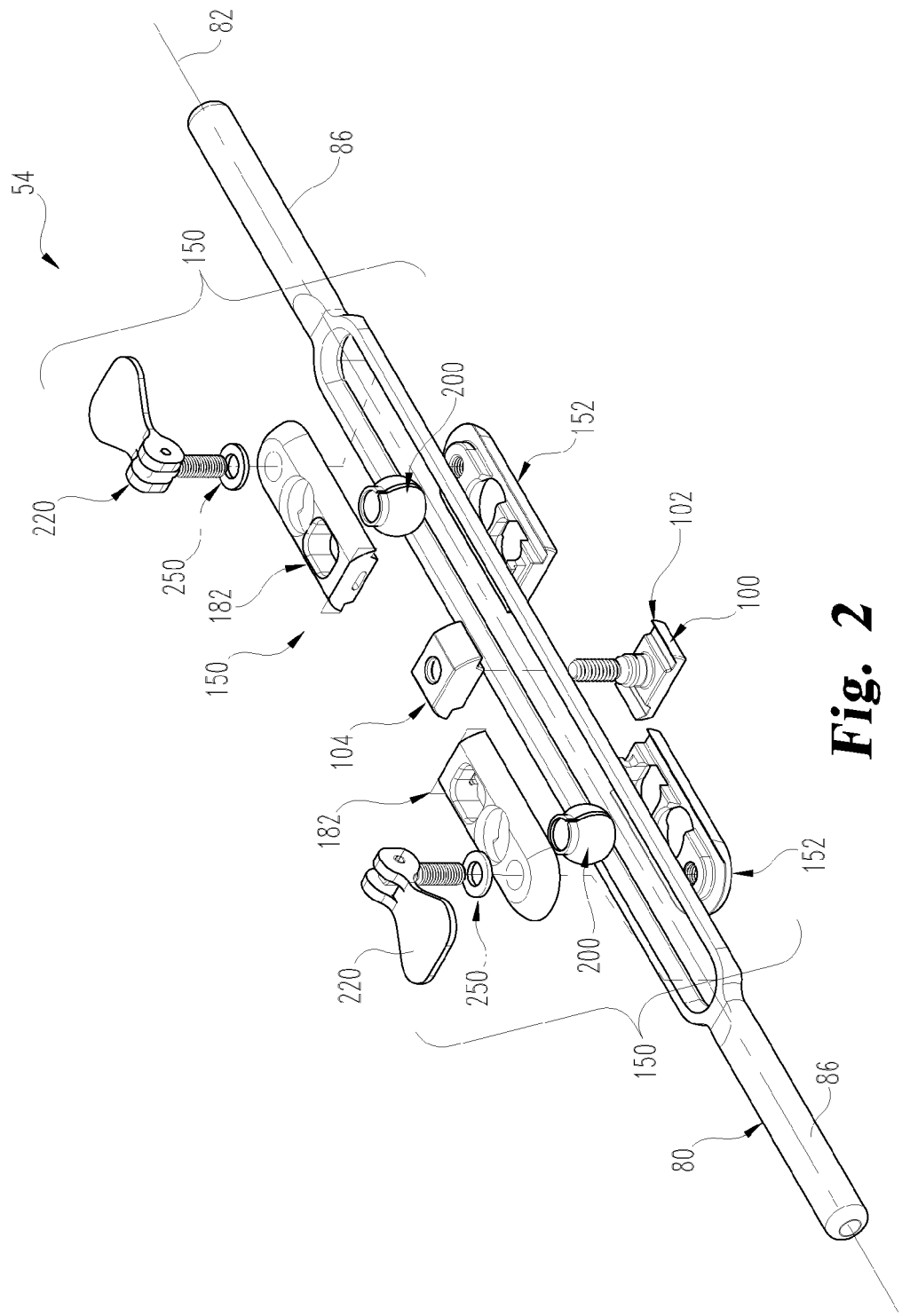
FIG. 2 is an exploded perspective view of an extension linking assembly of the derotation system of FIG. 1.

Referring now to FIG. 2, transverse linking assembly 54 is shown in an exploded perspective view. Linking assembly 54 includes an elongated link member 80 extending along a longitudinal axis 82. Linking assembly 54 further includes a handle mount 100 engaged to link member 80. Link assembly 54 also includes first and second mount assemblies 150 positioned on opposite sides of handle mount 100. Handle mount 100 and mount assemblies 150 are clampingly engaged to link member 80, and are releasable from clamping engagement with link member 80 and movable along axis 82 to adjust the relative position along link member 80. Each of the mount assemblies 150 houses a ball member 200 to form a movable joint in each mounting assembly 150 that receives coupling member 74 extending from a respective one of the anchor extensions 52. In addition, each of the mount assemblies 150 includes a cam assembly 220 that is operable to fix and release the respective mounting assembly 150 to link member 80 and to lock the movable joint in position in mounting assembly 150. Handle mount 100 and mount assemblies 150 can either be fixed or slidable along link member 80 and slidably repositioned along link member 80 to align with extensions 52 and clamped or otherwise secured in the new position.

Figure 3:
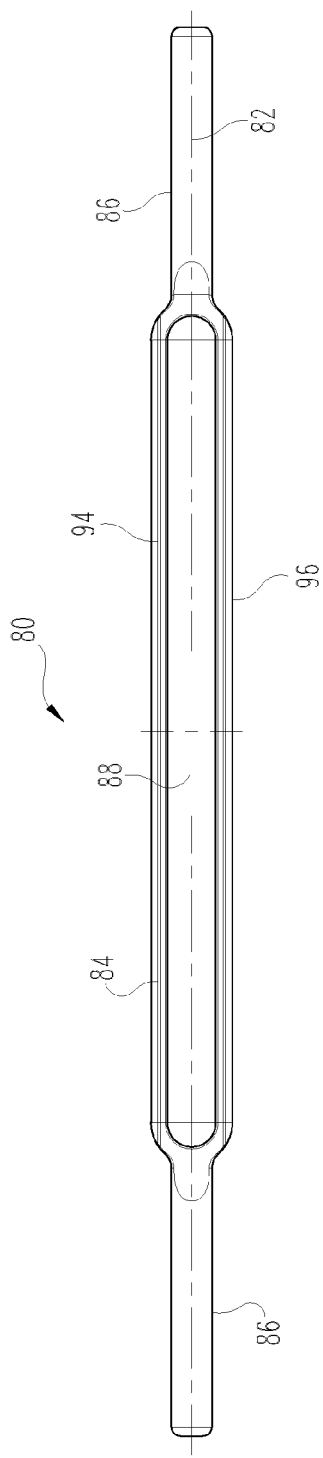
FIG. 3 is an elevation view of a plate of the extension linking assembly of FIG. 2.

Referring to FIG. 3, link member 80 is shown in isolation. Link member 80 extending along longitudinal axis 82 and includes a central plate portion 84 elongated along longitudinal axis 82 and opposite rod portions 86 extending axially away from opposite ends of plate portion 84. Central plate portion 84 includes an elongated center slot 88 opening at the upper and lower surfaces 90, 92 of central plate portion 84, and side members 94, 96 that extend along opposite sides of center slot 88. Plate portion 84 includes a generally rectangular shape in section that transitions to a circular shape in section along each of rod portions 86. Opposite rod portions 86 can be used as secondary handles 58, 60, and/or to mount an inter-level bridge to adjacent derotation instrumentation sets. The mounting assemblies 150 locate the ball joint on or adjacent to axis 82 and in center slot 88 so that members 74 of extensions 52 are engaged to link member 80 in slot 88. The assembly aligns the connections of the derotation handle 56 and extensions 52 to link member 80 along a common axis 82 where the longitudinal axes of handle 56 and extensions 52 intersect axis 82, eliminating bends or additional coupling mechanisms to align extensions 52 with link member 80.

Figure 5:
FIG. 5 is a center section view of a top portion of the handle mount of the extension linking assembly of FIG. 2.
Figure 4:
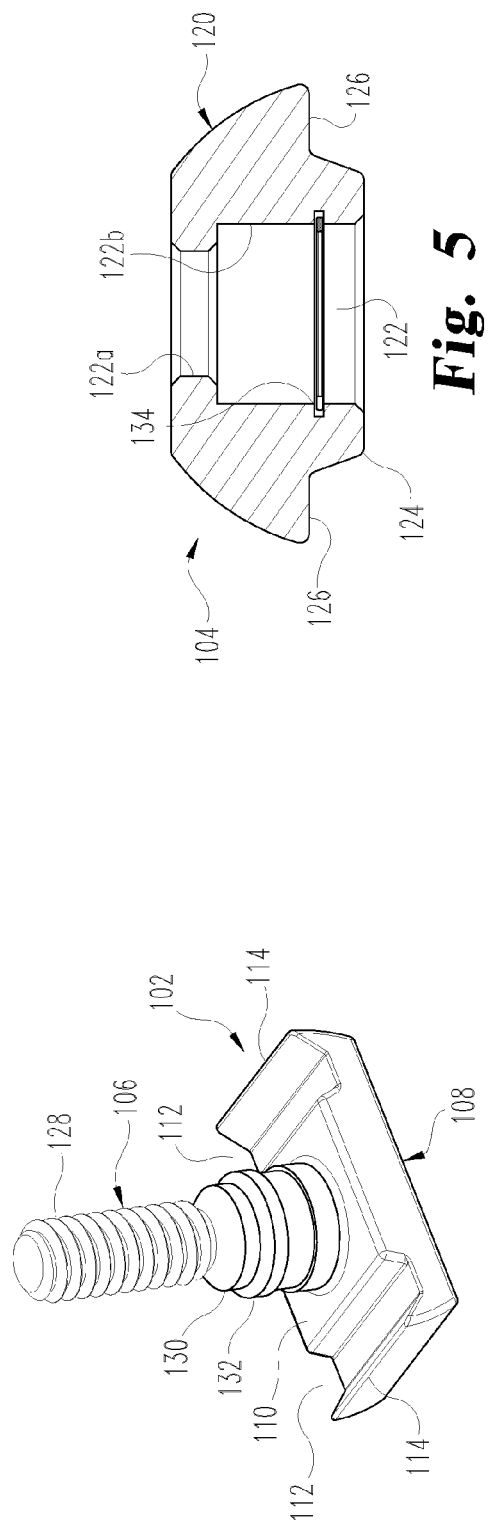
FIG. 4 is a perspective view of a bottom portion of the handle mount of the extension linking assembly of FIG. 2.
Figure 9:
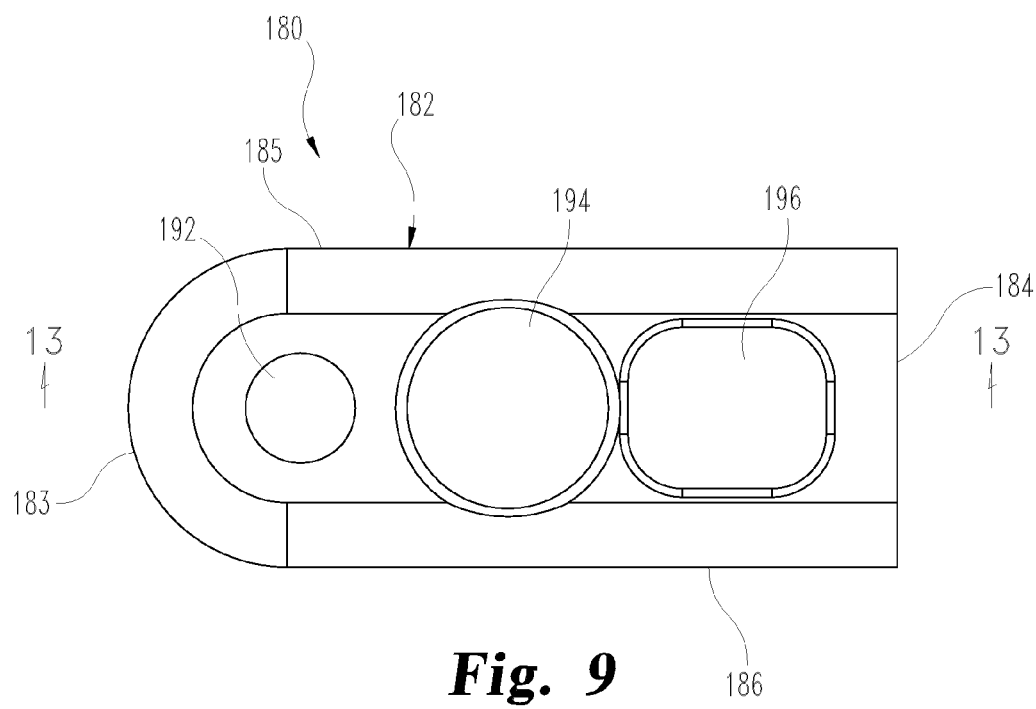
FIG. 9 is a plan view of the upper surface of the top plate of the extension linking assembly of FIG. 2.
Figure 10:
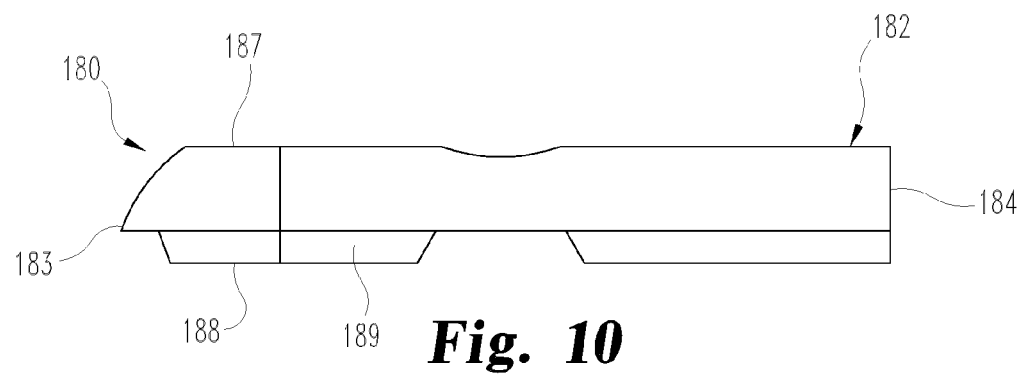
FIG. 10 is a side elevation view of the top plate of FIG. 9.
Figure 11:
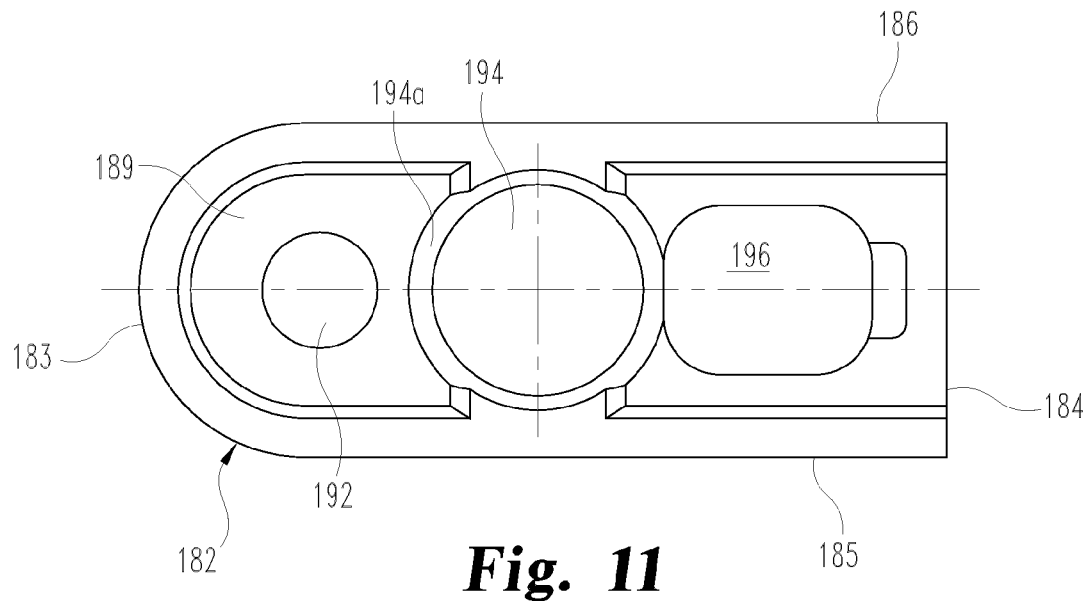
FIG. 11 is a plan view of the bottom surface of the top plate of FIG. 9.
Figure 12:
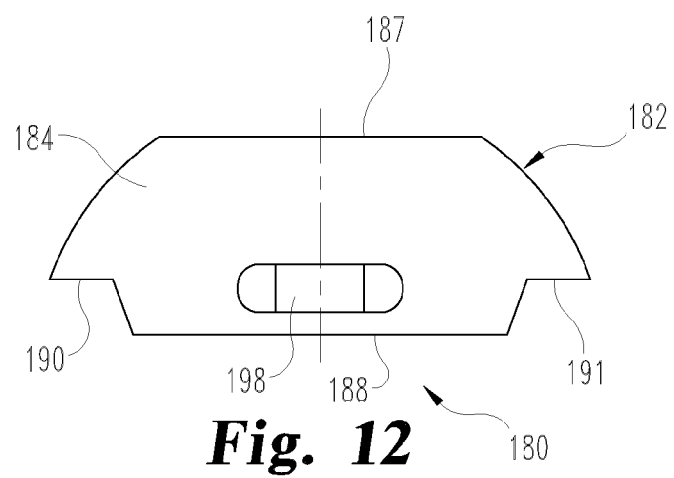
FIG. 12 is an end elevation view of the top plate of FIG. 9.

Handle mount 100 is further shown in FIGS. 4-5. Handle mount 100 includes a lower clamping member 102 and an upper clamping member 104. Link member 80 is positioned between clamping members 102, 104 with post 106 of lower clamping member 102 extending through center slot 88 and through upper clamping half 104. Derotation handle 56 is threadingly engaged to post 106 and threadingly movable along post 106 to selectively clamp and release halves 102, 104 of handle mount 100 to link member 80.

Lower clamping member 102 includes a plate member 108 extending outwardly from post 106. Plate member 108 includes a central portion 110, and grooves 112 extending along opposite sides of central portion 110. Lips 114 extend along opposite sides of grooves 112 on opposite sides of and offset from central portion 110. Grooves 112 receive respective ones of side members 94, 96 along lower surface 92 and capture side members 94, 96 between central portion 110 and lips 114, preventing twisting of lower clamping half 102 and handle mount 100 on link member 80. Upper clamping half 104 includes body portion 120 with a center hole 122 extending through upper and lower sides of body portion 120. Body portion 120 includes a central projecting portion 124 extending from the lower side thereof and opposite lips 126 extending outwardly from central projecting portion 124. Lips 126 extend along upper surface 90 of respective ones of side members 94, 96 and clamp against upper and lower surface 90, 92 of side members 94, 96 of link member 80 with lower clamping half 102. Central projecting portion 124 is received in slot 88 and also assists in preventing twisting of handle mount 100 relative to link member 80.

Post 106 is received through hole 122 of upper clamping half 104. Post 106 includes an upper threaded portion 128 and a lower non-threaded portion 130. Non-threaded portion 130 is cylindrical and extends from central portion 110 of plate member 108. Non-threaded portion 130 includes a retaining lip 132 projecting outwardly therefrom adjacent to upper threaded portion 128. When post 106 is positioned through center hole 122 of upper clamping half 104, threaded portion 128 extends through the reduced diameter portion 122a of hole 122 adjacent the upper side of body portion 120. Lower portion 130 is received in the larger diameter portion 122b of hole 122 opening at the lower side of clamping half 104. Clamping half 104 includes a c-clip or other retaining device 134 extending into portion 122b of hole 122 that contacts the lower side of retaining lip 132 to axially retain upper clamping half 104 on post 106. Clamping halves 102, 104 can axially translate or toggle relative to one another along post 106, allowing handle mount 100 to be selectively clamped and released with link member 80. Derotation handle 56 is threadingly engaged to threaded portion 128 and is threaded distally along threaded portion 128 to contact upper clamping half 104 and press lower clamping half 102 and upper clamping half 104 against side members 94, 86 of link member 80, such as shown in FIG. 1.

In one embodiment, derotation handle 56 includes an elongate hollow cylindrical-type body extending between a proximal end 56a and a distal end 56b. The body includes an internally threaded passage to engage threaded portion 128 of post 106. Other coupling arrangements between derotation handle 56 and post 106 are also contemplated, including non-threaded coupling arrangement, snap fits, interference fits, supplemental connectors such as a set screw, clamping arrangements, bayonet locks, and integral connections, for example. Distal end 56b contacts upper clamping half 104 to secure clamping halves 102, 104 against link member 80, such as shown in FIG. 1. When derotation handle 56 is threaded along post 106, as indicated by arrow 57 in FIG. 20, distal end 56b can be spaced proximally from upper clamping half 104, such as shown in FIG. 20, or moved distally to be positioned against upper clamping half 104 as shown in FIG. 2. Handle mount 100 can translate along side members 94, 96 for repositioning of derotation handle 56.

Each of the mounting assemblies 150 includes a lower plate member 152 and an upper plate member 180 pivotally coupled to lower plate member 152. Each of the mounting assemblies 150 also includes ball member 200 housed between plate members 152, 180 that forms a ball joint in each mounting assembly 150 that receives member 74 extending from a respective one of the extensions 52. Each of the mounting assemblies 150 also includes a cam assembly 220 attached to lower plate member 152 and selectively positionable into contact with upper plate member 180 to move plate members 152, 180 toward one another, clamping link member 80 between plate members 152, 180 and securing ball member 200 around member 74 of the extension positioned in ball member 200. FIGS. 6-8 show further details of lower plate member 152, and FIGS. 9-13 show further details of upper plate member 180.

Lower plate member 152 includes an elongated plate body 154 extending between a rounded first end 155 and an opposite linear second end 156. Body 154 includes opposite sidewalls along sides 158, 160 extending between opposite endwalls at ends 155, 156. Body 154 includes a flat lower surface 162 and an opposite upper surface 164 with a central projecting portion 166 and rails 168, 170 extending along respective ones of sides 158, 160. Grooves 172, 174 extend between respective ones of rails 168, 170 and central projecting portion 166 and receive a lower portion of side members 94, 96 of link member 80 therein.

Lower plate member 152 also includes a threaded hole 176 adjacent to first end 155 that extend between lower surface 162 and upper surface 164 along central projecting portion 166. Lower plate member 152 further includes a ball joint receptacle 178 extending through and opening at lower surface 162 and upper surface 164. Receptacle 178 includes inwardly tapering sidewall 178a that forms a lip 178b recessed slightly below upper surface 164 and a compression surface 178c that extends proximally from lip 178b to upper surface 164 that supports a lower part of ball member 200 thereon between plate members 152, 180. Compression surface 178c extends along the portions of central projecting portion 166 located centrally along receptacle 178, and is interrupted by grooves 172, 174 on the opposite sides of plate member 152. Sidewall 178a angles outwardly in the distal direction and opens through lower surface 162 to provide clearance for member 74 at various angles through plate member 152 and ball member 220. Lower plate member 152 also includes a through-hole 179 extending therethrough opening at upper and lower surfaces 164, 162 that is situated between second end 156 and receptacle 178. Projecting portion 166 includes a hook member 167 extending outwardly from upper surface 164 that is hooked toward second end 156.

Upper plate member 180 includes an elongated plate body 182 extending between a rounded first end 183 and an opposite linear second end 184. Body 182 includes sidewalls along opposite sides 185, 186 extending between opposite endwalls at ends 183, 184. Body 182 includes a generally flat upper surface 187 and an opposite lower surface 188 with a central projecting portion 189 and lips 190, 191 extending along respective ones of sidewalls 185, 186. As shown in FIG. 20A, lips 190, 191 are positioned toward the upper surface 90 of side members 94, 96 of link member 80 to secure link member 80 between plate members 152, 180. Central projecting portions 166, 189 of plate members 152, 180 extend into slot 88 of link member 80 to prevent twisting of mounting assembly 150 relative to link member 80 and assist in locating plate members 152, 180 relative to link member 80.

Upper plate member 180 also includes a non-threaded hole 192 adjacent to first end 183 that extends between and opens at lower surface 188 along central projecting portion 189 and upper surface 187. Hole 192 aligns with threaded hole 176 of lower plate member 152. Upper plate member 180 further includes a ball joint receptacle 194 extending through and opening at lower surface 188 and upper surface 187. Receptacle 194 includes inwardly tapering sidewalls 194a that form a lip 194b recessed slightly below upper surface 187 that contacts an upper or proximal portion of ball member 200 located between plate members 152, 180. Receptacle 194 also includes outwardly angled surface portion 194c to provide clearance for pivoting of collar 210 of ball member 200. Upper plate member 180 also includes a through-hole 196 extending therethrough opening at upper and lower surfaces 187, 188 that is situated between second end 184 and receptacle 194. Projecting portion 189 includes a hook receptacle 198 that opens through the end wall at second end 184 and extends into through-hole 196. When plate members 152, 180 are assembled, hook member 167 is received in through-hole 196 and into receptacle 198 to releasable pivotally couple second ends 156, 184 to one another, allowing first ends 154, 183 to move toward and away from one another about hook member 167 to selectively clamp and release side members 194, 196 of link member 80 between plate members 152, 180.

Referring now to FIGS. 14-16, ball member 200 is show in isolation. Ball member 200 includes a spherical body 202 with an axial passage 204 extending therethrough and opening at upper and lower sides of body 202. Body 202 also includes a longitudinal slot 206 extending along one side thereof that opens into passage 204. Body 202 includes a convexly rounded outer surface 208 extending therearound and a cylindrical collar 210 extending from the upper end thereof. As lips 178b and 194b of plate members 152, 180 move along outer surface 208, body 202 is radially movable to open slot 206 or to close slot 206 to clamp ball member 200 against an outer surface of member 74 when member 74 is positioned in passage 204. Body portion 202 forms a living or integral hinge 212 opposite slot 206 to facilitate clamping engagement of ball member 200 against member 74.

Figure 17:
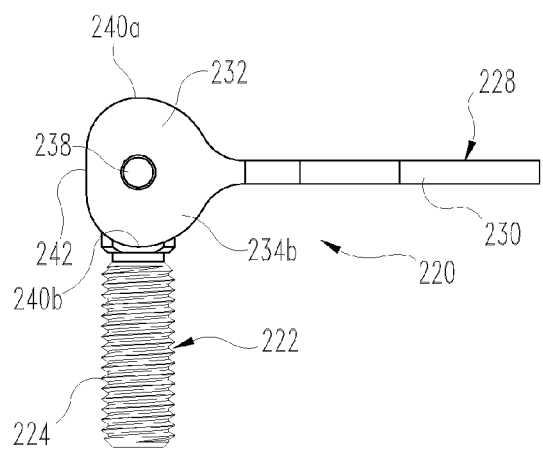
FIG. 17 is a side elevation view of a cam assembly in an engaged position.
Figure 18:
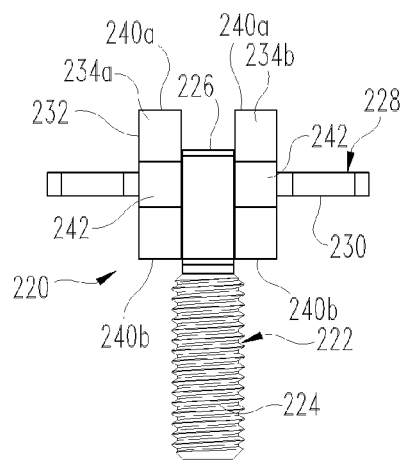
FIG. 18 is a side elevation view of the cam assembly of FIG. 17.
Figure 19:
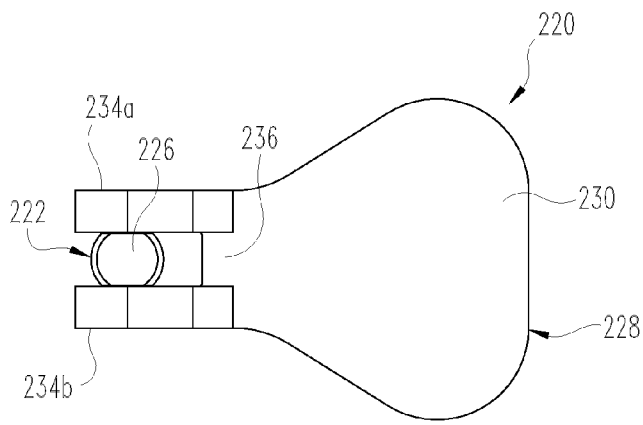
FIG. 19 is an elevation view of the cam assembly of FIG. 17.

FIGS. 17-19 show cam assembly 220 in isolation. Cam assembly 220 includes a post 222 with a lower threaded portion 224 and an upper mounting portion 226. Lower portion 224 includes a cylindrical shape with an outer thread profile that threadingly engages lower plate of mounting assembly 150 with mounting portion 226 positioned adjacent the upper side of upper plate member 180 of mounting assembly 150. Cam assembly 220 also includes a cam latch 228 with a handle portion 230 and a cam portion 232. Cam portion 232 includes a pair of cam members 234a, 234b separated from one another by slot 236. A pin 238 extends through cam members 234a, 234b and upper mounting portion 226 in slot 236 to pivotally couple cam latch 228 to post 222. Handle portion 230 includes a flat plate-like shape that extends transversely to and projects outwardly from cam members 234a, 234b to provide a platform for grasping by the surgeon or other user to pivot cam latch 228 about pin 238 relative to post 222.

Each of the cam members 234a, 234b includes an oblong shape with a major dimension extending between cam surfaces 240a, 240b and a minor dimension extending from pin 238 to side 242. The minor dimension is less than one half of the major dimension so that when side 242 is oriented toward upper plate of mounting assembly 150 side 242 is spaced a distance d from spacer 250 of mounting assembly 150 as shown in FIG. 20. In this position, mounting assembly 150 is unclamped from link member 80 and can slide or translate as indicated by bi-directional arrow T along mounting assembly 150. When handle portion 230 of latch assembly 220 is pivoted as indicated by arrow P to the position shown in FIG. 1, one of cam surfaces 240a, 240b is positioned in contact with spacer 250 adjacent upper surface 187 of upper plate member 180 of mounting assembly 150. The aligned cam surface 240a, 240b forces spacer 250 against the proximal surface of plate member 180 and pivots plate members 152, 180 about hook member 167, positioning plate members 152, 180 into clamping engagement with ball member 200 and link member 80 and securing the mounting assembly 150 in position along link member 80. In one embodiment the ball member is permanently captured between the plate members 152, 180 by securing cam assembly 220 to plates 152, 180 to prevent disassembly without damaging the mounting assembly 150.

In another embodiment, mounting assemblies 150 can be readily disassembled by moving handle portion 230 to the unlatched position, and unthreading post 222 from lower plate member 152 so that hook member 267 can be displaced laterally from receptacle 198, allowing plate member 152, 180 to separate from one another.

Figure 20B:
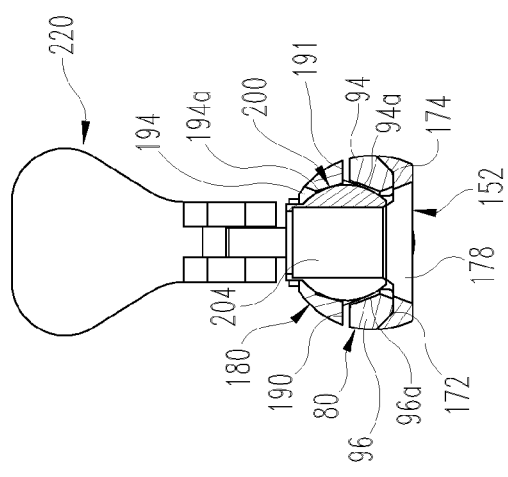
FIG. 20B is a section view along line 20B-20B of FIG. 20.

FIG. 20B shows ball member 200 positioned between plate members 152, 180 of mounting assembly 150 and link member 80. In particular, lower plate member 152 is positioned below or distally of side members 94, 96 of link member 80 with side members 94, 96 received in respective ones of the grooves 172, 174. Ball member 200 is supported on inner surfaces 94a, 96a of side members 94, 96 and in alignment with receptacle 178 of lower plate member 152. Surfaces 94a, 96a converge distally and contact outer surface 208 of ball member 200 along the lower half of ball member 200. As shown in FIGS. 6 and 8, receptacle 178 includes proximal and outwardly angled compression surfaces 178c on central projecting portion 166 that contact ball member 220 on axis 82 and across slot 88 of link member 80. Thus, link member 80 and lower plate 152 together support the lower portion of ball member 200 in mounting assembly 150.

Upper plate member 180 includes compression surface 194a extending completely around receptacle 194 that contacts the upper half of ball member 200. When cam assembly 220 is pivoted to the engaged position, plate member 180 pivots around hook member 167 and ball member 200 is compressed between compression surface 194a against the upper or proximal side of ball member 200 and compression surface 178c of lower plate 152 and inner surfaces 94a, 96a of link member 80 against the lower or distal side of ball member 200.

Figure 21:
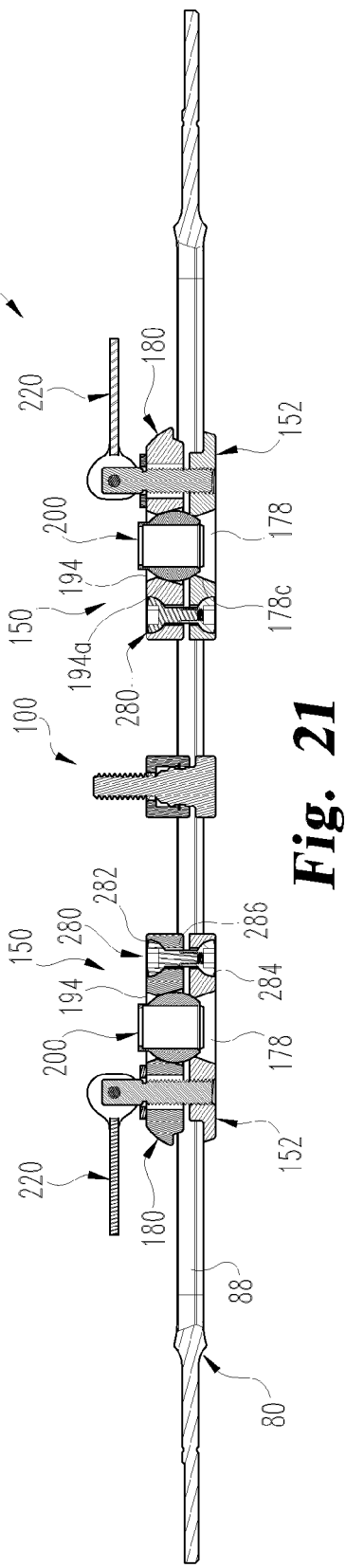
FIG. 21 is a longitudinal section view of the linking assembly with another embodiment connection between the upper and lower plates of the mounting assemblies.

FIG. 21 shows a longitudinal section view of the derotation linking assembly 54 with another embodiment connection mechanism between plates 152, 180 of mounting assemblies 150. In FIG. 21, plates 152, 180 are pivotally coupled to one another with a connector 280 including a shaft 286 extending between plate members 152, 180 adjacent first ends 183, 155. Spherical heads 282, 284 are attached to opposite ends of shaft 286 and are received in respective one of spherical recesses of plates 152, 180 adjacent to first ends 155, 183. The spherical heads 282, 284 allow pivoting movement of plates 152, 180 relative to one another about first ends 155, 183.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion. In addition, various portions of the instrumentation are described herein with reference to an "upper" or "lower" arrangement. The terms "upper" and "lower" refer to the arrangements illustrated in the Figures and are not intended to be limiting as to relative locations between or orientations of the components of the instrumentation.

While the invention has been illustrated and described in detail in the drawings and foregoing description, the same is to be considered as illustrative and not restrictive in character. All changes and modifications that come within the spirit of the invention are desired to be protected.

What is claimed is:

1. A system for correcting alignment of one or more vertebrae of a spine, comprising:
   first and second implants engageable to at least one vertebra, said first and second implants being configured for engagement with at least one elongated stabilization element positionable along the one or more vertebrae of the spine;
   a derotation instrument set including:
   first and second elongated implant extensions with distal end portion releasably engaged to respective ones of said first and second implants, said implant extensions each extending from said distal end portion thereof to an opposite proximal end portion;
   a transverse linking assembly positioned between and engaged to said first and second implant extensions at said proximal end portions, said transverse linking assembly including an elongate link member with a central plate portion extending between said proximal end portions of said implant extensions, said linking assembly further including a derotation handle engaged to said central plate portion and first and second mounting assemblies engaged to said central plate portion and to said proximal end portion of a respective one of said first and second implant extensions, said mounting assemblies each including first and second plate members along opposite sides of said central plate portion and a pivotable ball member captured between said first and second plate members that receives said proximal end portion of a respective one of said extensions;
   said first and second plate members each include opposite sides that extend from a first end wall to an opposite second end wall, said first end of said first plate member including a receptacle opening at said first end wall and said first end of said second plate member including a hook member positioned in said receptacle to pivotally couple said first ends of said first and second plate members to one another; and
   wherein each of said first and second mounting assemblies includes a cam assembly adjacent said second ends of said first and second plate members, said cam assembly having a first position wherein said first and second plate members are released from said side members to allow said mounting assembly to translate along said central plate portion and said cam assembly is movable to a second position wherein said cam assembly forces said first and second plate members and said central plate portion into clamping engagement with said ball member.

2. The system of claim 1, wherein said central plate portion includes a pair of side members extending between opposite ends of said plate portion on opposite sides of a central slot of said plate portion, and said ball member is clampingly engaged to said side members of said plate portion with said first and second plate members.

3. The system of claim 1, wherein said first plate member includes a non-threaded hole and said second plate member includes a threaded hole aligned with said non-threaded hole and said cam assembly includes a post threadingly engaged with said threaded hole and extending through said non-threaded hole, said cam assembly further including a latch with a proximal handle portion and a distal cam portion pivotally mounted to a proximal portion of said post, said cam portion including a first surface portion spaced from said first plate member in said first position and a cam surface portion oriented toward said first plate member in said second position, said cam portion being rotatable about said proximal portion of said post to position said cam portion toward said first plate member and force said first plate member toward said second plate member when said cam assembly is in said second position.

4. The system of claim 3, wherein said first plate member includes a spacer positioned between said cam portion of said latch and a proximal surface of said first plate member.

5. The system of claim 1, wherein:
said first plate member includes a first receptacle with an inwardly tapering sidewall extending around said first receptacle that forms a first lip within said first receptacle;
said second plate member includes a second receptacle with an inwardly tapering sidewall extending around said second receptacle that forms a second lip within said second receptacle, said first and second receptacles being aligned with one another; and
said ball member is positioned in said first and second receptacles in contact with said inwardly tapering sidewalls and said central plate portion of said link member, said inwardly tapering sidewalls and said central plate portion of said link member contacting an outer surface of said ball member to compress said ball member around said proximal end portion of said respective extension.

6. The system of claim 1, wherein said first and second extensions each include:
an elongate inner member includes a pair of arms forming said distal portion of said extension; and
an outer tubular member positioned around said inner member in contact with said pair of arms to engage said pair of arms with said respective one of said first and second implants.

7. The system of claim 1, wherein:
said elongate link member includes a central slot and a pair of side members extending along opposite sides of said central slot; and
said first and second plate members of each of said mounting assemblies include central projecting portion positioned in said slot, and one of said first and second plate members includes a pair of grooves extending along said central projecting portion thereof and said pair of side members are located in respective ones of said pair of grooves, and said ball member includes a distal portion in contact with said pair of said side members and said central projecting portion of said one of said first and second plates receiving said pair of side members in said pair of grooves, and said ball member includes a proximal portion in contact with the other of said first and second plate members.

8. A system for correcting alignment of one or more vertebrae of a spine, comprising:
first and second implants engageable to at least one vertebra, said first and second implants being configured for engagement with at least one elongated stabilization element positionable along the spine;
a derotation instrument set including:
first and second elongated implant extensions with distal end portions releasably engaged to respective ones of said first and second implants, said implant extensions each extending from said distal end portion thereof to an opposite proximal end portion;
a transverse linking assembly positioned between and engaged to said first and second implant extensions at said proximal end portions, said transverse linking assembly including an elongate link member with a slot and a pair of side members extending along opposite sides of said slot, said linking assembly further including a derotation handle engaged to said link member along said slot and first and second mounting assemblies engaged to said link member on opposite sides of said derotation handle, said first and second mounting assemblies each including a pivotable joint in said slot receiving said proximal end portion of a respective one of said first and second implant extensions through said slot of said link member;
each of said mounting assemblies includes first and second plate members positioned along opposite sides of said pair of side members of said link member and said pivotable joint includes a ball member captured between said first and second plate members, said ball member including a passage that receives said proximal end portion of said respective extension;
said first and second plate members of said mounting assemblies each include opposite sidewalls that extend from a first end wall to an opposite second end wall, said first end wall of said first plate member including a receptacle opening at said first end wall and said first end of said second plate member including a hook member positioned in said receptacle to pivotally couple said first ends of said first and second plate members to one another;
said mounting assemblies further includes a cam assembly adjacent said second ends of said first and second plate members, said cam assembly including a first position wherein said first and second plate members are released from said side members of said link member to allow said mounting assembly to translate along said side members and said cam assembly is moved from said first position to a second position wherein said cam assembly forces said first and second plate members and said link member into clamping engagement with said ball member.

9. The system of claim 8, wherein said first plate includes a non-threaded hole and said second plate includes a threaded hole aligned with said non-threaded hole and said cam assembly includes a post threadingly engaged with said threaded hole extending through said non-threaded hole, said cam assembly further including a latch with a proximal handle portion and a distal cam portion pivotally mounted to a proximal portion of said post, said cam portion including a first surface portion spaced from said first plate member in said first position and said cam portion being rotatable about said proximal portion of said post to position a cam surface portion of said cam portion toward said first plate member to force said first and second plate members toward one another when said cam assembly is in said second position.

10. The system of claim 8, wherein each of said first and second plate members of said mounting assemblies includes a central projecting portion positioned in said slot, and one of said first and second plate members includes a pair of grooves extending along said central projecting portion thereof and said pair of said side members include a first surface located in respective ones of said pair of grooves.

11. The system of claim 8, wherein each of said mounting assemblies includes first and second plate members positioned along opposite sides of said link member and each of said first and second plate members includes a rounded first end wall and an opposite linear second end wall, said first and second end walls extending between opposite sidewalls that extend along said side members of said link member, and said first plate member defines a non-threaded hole and said second plate member defines a threaded hole aligned with said non-threaded hole adjacent said first end walls of said first and second plate members, and said first and second plate members define aligned through-holes adjacent said second end walls of said first and second plate members, and said first and second plate members define aligned receptacles located between said aligned through-holes and said aligned non-threaded and threaded holes, and further comprising: a cam assembly with a post extending through said non-threaded hole and threadingly engaged to said threaded hole, said cam assembly including a cam member mounted to said post that is movable relative to said post to move said first and second plate members toward one another; a ball member captured in said aligned receptacles of said first and second plate members in contact with each of said first and second plate members and in contact with opposite side members of said link member; and a hook member extending from said second plate member into said through-hole of said first plate member, said hook member further extending into a slot extending from said through-hole of said first plate member through said second end wall of said first plate member to pivotally couple said first and second plate members to one another about said hook member.

12. A system for correcting alignment of one or more vertebrae of a spine, comprising:
first and second implants engageable to at least one vertebra, said first and second implants being configured to receive an elongate stabilization element positionable along the vertebrae of the spine;
a derotation instrument set including:
first and second elongated implant extensions with distal end portions releasably engageable to respective ones of said first and second implants, said implant extensions each extending from said distal end portion thereof to an opposite proximal end portion;
a transverse linking assembly positioned between and engaged to each of said first and second implant extensions at said proximal end portions, said transverse linking assembly including an elongate link member with a central slot, a derotation handle engaged to said link member along said slot, and first and second mounting assemblies engaged to said link member on opposite sides of said derotation handle, said first and second mounting assemblies each including first and second plate members engaged to opposite sides of said link member along said slot, wherein:
said first and second plate members each include a first end wall and an opposite second end wall, said first and second end walls extending between opposite sidewalls of said plate member positioned along said link member, said first plate member defines a non-threaded hole and said second plate member defines a threaded hole aligned with said non-threaded hole adjacent said first end walls of said first and second plate members, said first and second plate members define aligned through-holes adjacent said second end walls of said first and second plate members, and said first and second plate members define aligned receptacles located between said aligned through-holes and said aligned non-threaded and threaded holes;
a ball member is captured between said first and second plate members in said aligned receptacles, and a proximally extending member of a corresponding one of said extensions is positioned in said ball member;
a hook member extends from said second plate member into said through-hole of said first plate member, said hook member further extending into a slot extending from said through-hole of said first plate member through said second end wall of said first plate member, said hook member pivotally coupling said first and second plate members to one another; and
a cam assembly includes a post extending through said non-threaded hole and threadingly engaged to said threaded hole, said cam assembly further including a cam member mounted to said post and said cam member includes a cam surface positionable to pivot said first and second plate members about said hook and force said first and second plate members and said link member into contact with said ball member and compress said ball member around said proximally extending member of said one extension.

13. The system of claim 12, wherein for each of said first and second plate members said first end wall is rounded between said sidewalls and said second end wall is linear between said sidewalls.

* * * * *